United States Patent
Santosh et al.

(10) Patent No.: US 9,322,895 B2
(45) Date of Patent: Apr. 26, 2016

(54) METHOD OF DETERMINING METABOLIC FUNCTION USING MAGNETIC RESONANCE SPECTROSCOPIC IMAGING

(75) Inventors: Celestine Santosh, Glasgow (GB); William Holmes, Glasgow (GB); Rosario Lopez, Glasgow (GB)

(73) Assignees: Greater Glasgow Health Board, Glasgow (GB); The University Court of the University of Glasgow, Glasgow (GB)

( * ) Notice: Subject to any disclaimer, the term of this patent is extended or adjusted under 35 U.S.C. 154(b) by 636 days.

(21) Appl. No.: 13/394,212

(22) PCT Filed: Sep. 3, 2010

(86) PCT No.: PCT/GB2010/051466
§ 371 (c)(1),
(2), (4) Date: May 16, 2012

(87) PCT Pub. No.: WO2011/027165
PCT Pub. Date: Mar. 10, 2011

(65) Prior Publication Data
US 2012/0219507 A1  Aug. 30, 2012

(30) Foreign Application Priority Data
Sep. 4, 2009 (GB) .................................. 0915464.2

(51) Int. Cl.
*A61B 5/055* (2006.01)
*G01R 33/483* (2006.01)
*A61B 5/00* (2006.01)
(Continued)

(52) U.S. Cl.
CPC ............. *G01R 33/483* (2013.01); *A61B 5/055* (2013.01); *A61B 5/4076* (2013.01); *A61B 5/415* (2013.01); *A61B 5/418* (2013.01); *G01N 24/08* (2013.01); *G01N 24/088* (2013.01); *G01R 33/4828* (2013.01); *A61B 5/4088* (2013.01); *A61B 5/4094* (2013.01); *G01R 33/5601* (2013.01); *G01R 33/5607* (2013.01); *G01R 33/5617* (2013.01);
(Continued)

(58) Field of Classification Search
CPC .... A61B 5/055; A61B 5/4076; A61B 5/4088; A61B 5/4094; A61B 5/415; A61B 5/418; G01N 24/08; G01N 24/088; G01R 33/4828; G01R 33/483; G01R 33/5601; G01R 33/5607; G01R 33/5617; G01R 33/56341; G01R 33/56366
See application file for complete search history.

(56) References Cited

U.S. PATENT DOCUMENTS

2005/0240096 A1* 10/2005 Ackerman et al. ............. 600/410
2006/0142983 A1*  6/2006 Sorensen et al. ................ 703/11
(Continued)

OTHER PUBLICATIONS

Cudalbu, et al., "Brain metabolite concentration estimates using Magnetic Resonance Spectroscopy in a chronic model of temporal lobe epilepsy", C.R. Chome 11 (2008) 434-441.
(Continued)

*Primary Examiner* — Ruth S Smith
(74) *Attorney, Agent, or Firm* — Drinker Biddle & Reath LLP

(57) ABSTRACT

The present invention provides a novel lactate difference imaging (LDI) technique, allowing assessment of the metabolic responses of tissue over a period of time. This approach utilizes lactate change over a time period as an indicator of viable tissue, and offers benefits in the management and treatment of the effects of many common diseases, in particular stroke.

15 Claims, 8 Drawing Sheets

Lac/Lip before Oxygen

Lac/Lip during Oxygen

(51) Int. Cl.
*G01N 24/08* (2006.01)
*G01R 33/48* (2006.01)
*G01R 33/56* (2006.01)
*G01R 33/561* (2006.01)
*G01R 33/563* (2006.01)

(52) U.S. Cl.
CPC ..... *G01R 33/56341* (2013.01); *G01R 33/56366* (2013.01)

(56) References Cited

U.S. PATENT DOCUMENTS

| | | | |
|---|---|---|---|
| 2009/0027051 A1* | 1/2009 | Stuber et al. | 324/309 |
| 2009/0209831 A1* | 8/2009 | Kucharczyk et al. | 600/301 |
| 2009/0246138 A1* | 10/2009 | Santosh et al. | 424/9.2 |
| 2009/0247860 A1* | 10/2009 | Djuric et al. | 600/420 |

OTHER PUBLICATIONS

Reinert, et al., "Effects of cerebral perfusion pressure and increased fraction of inspired oxygen on brain tissue oxygen, lactate and glucose in patients with severe head injury", *Acta Neurochir* (2003) 145: 341-350.

Santosh, et al., "Potential use of oxygen as a metabolic biosensor in combination with T2*-weighted MRI to define the ischemic penumbra", Journal of Cerebral Blood Flow & Metabolism (2008) 28, 1742-1753.

* cited by examiner

Fig 2a.
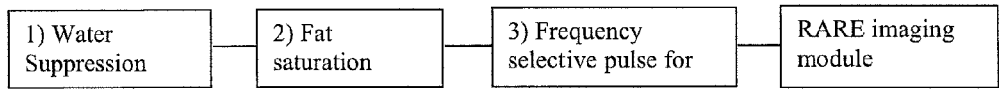
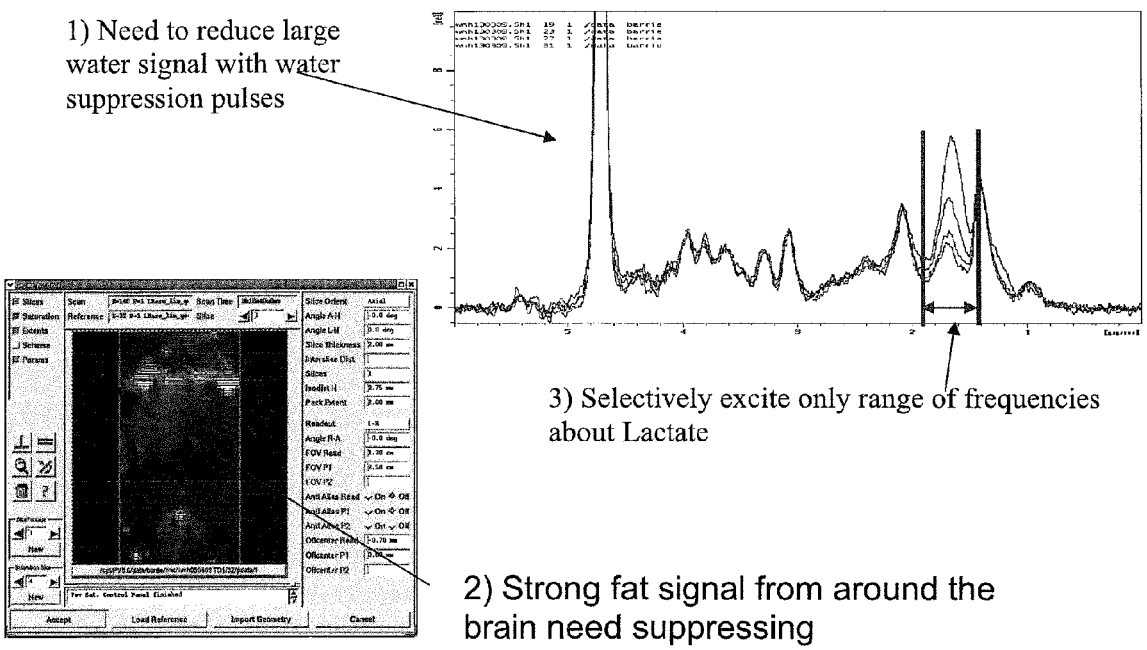
Fig 2b.
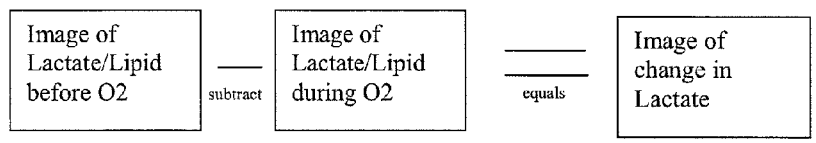
Figure 2 full ¹H water signal. (high signal from all)

Lactate $CH_3$ signal. No signal from water.

Fig 6a.
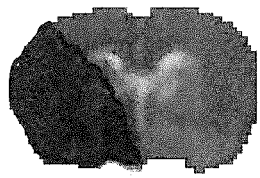
Fig 6b.
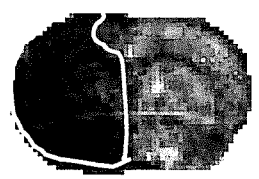
Fig 6c.
Baseline
Fig 6d.
20 min oxygen
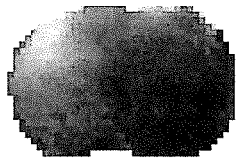
Fig 6e.
20 min Air
Fig 6f.
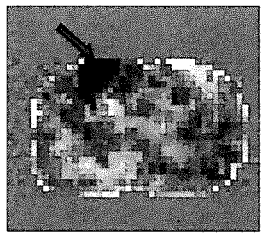
Fig 6g.
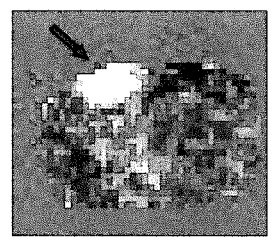
Figure 6.

Fig 9a.
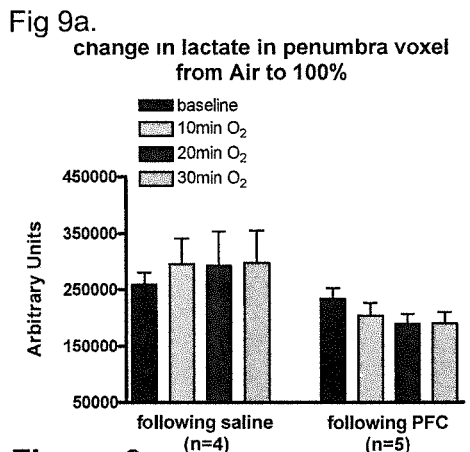
Fig 9b.
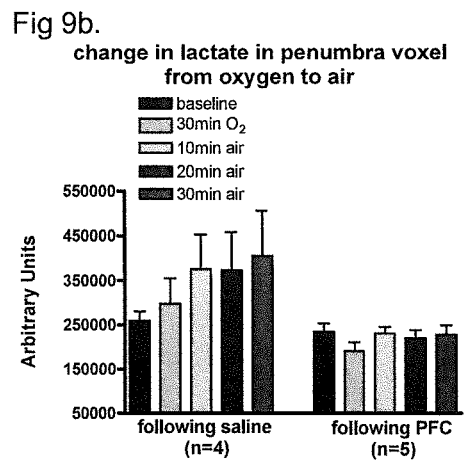
Figure 9.
Fig 10a.
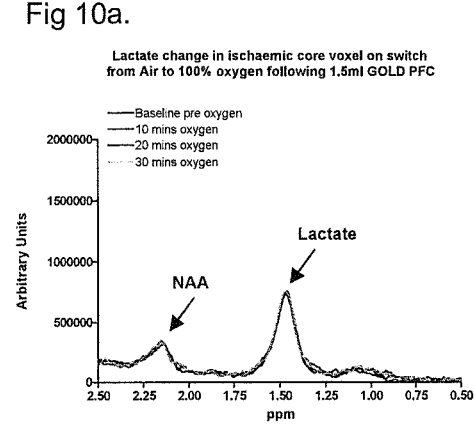
Fig 10b.
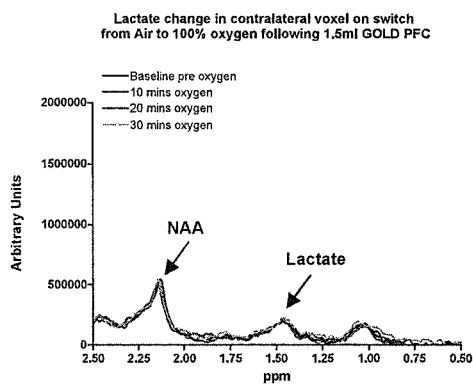
Figure 10.

US 9,322,895 B2

METHOD OF DETERMINING METABOLIC FUNCTION USING MAGNETIC RESONANCE SPECTROSCOPIC IMAGING

FIELD OF THE INVENTION

The present invention relates to an improved method for determining metabolic function in an organism.

BACKGROUND OF THE INVENTION

The concept of the ischemic penumbra is now more than 20 years old. Following occlusion of a brain artery some of the brain tissues supplied by the vessel perish due to hypoxia/anoxia but some tissues have a capability to recover with appropriate treatment. Astrup first defined ischemic penumbra in 1981 as perfused brain tissue at a level within the thresholds of functional impairment and morphological integrity, which has the capacity to recover if perfusion is improved. This happens due to the inability of cells to produce ATP (energy) leading to cell dysfunction and then cell death. Therefore any technique demonstrative of active metabolism within the affected tissues would also be able to detect the penumbra.

SUMMARY OF THE INVENTION

The invention to be more particularly described hereinafter utilizes in one aspect in-vivo MRI contrast imaging utilising a novel lactate difference imaging (LDI) technique, together with an oxygen challenge, to provide imaging for the assessment of the metabolic responses of tissue over a period of time. Hitherto, the value of quantifying cellular lactate distribution over a measured time period has not been recognised as an indicator of metabolic function. Surprisingly, current work has demonstrated that areas of viable tissue which are at risk of suffering irreversible damage may be rapidly identified and located with a high degree of accuracy by measuring lactate concentration over a defined time period. Therefore, according to an aspect of the invention, a preliminary lactate evaluation of a target tissue provides an indication of metabolic activity within the tissue.

According to a further aspect, the proposed lactate evaluation is also combined with an oxygen challenge. This approach permits the discrimination of lactate usage over a time period of evaluation of tissue metabolism which is not possible using hitherto published techniques. Thereby, oxygen use as contemplated herein with MRI imaging can be utilized as an indicator of viable tissue, which offers benefits in the management and treatment of the effects of many common diseases, in particular stroke.

According to an aspect of the present invention, there is provided a method of imaging metabolic function in a target area of an organism using contrast magnetic resonance imaging (MRI), the method comprising the steps of: i) obtaining a first measurement of lactate in a target area of the organism; ii) administering oxygen to said organism; iii) obtaining a second measurement of lactate in a target area of the organism following said administration of oxygen; iv) comparing said first and second measurements to obtain data relating to the relative amounts of lactate present in said target area before and following administration of the oxygen, and correlating said data to the metabolic function of the target area.

Preferably, the step of correlating said data to the metabolic function of the target area includes processing the data to assess said metabolic function.

Preferably, obtaining a measurement of lactate comprises obtaining one or more MRI images of the target area.

The data obtained by the method of the first aspect may provide a semi-quantitative measurement of lactate which reveals metabolic function information. Here, lactate concentration over time, provides the variable parameter which can be utilized in the imaging evaluation.

Following cerebral infarction, lactate has been shown by MR spectroscopy to accumulate in the oxygen-starved tissue surrounding the area of infarction, due to failure of aerobic metabolism (Berkelback van der Sprenkel J W et al 1988, Fenstermacher M J and Naryana P A 1990 and Houkin K 1990).

It is considered that the preferred substrate for neuronal metabolism is lactate, which is produced primarily by the astrocytes.

Oxygen challenge is utilised as a metabolic biotracer (for presence of aerobic metabolism) in target tissues. Therefore, the method can be used to produce a metabolic map of a target area in the body.

The oxygen administered to the organism allows the reinitiation of aerobic metabolism in the cells of the ischaemic lesion, characterised by the utilisation of lactate as the substrate for aerobic oxidation local by neurons.

The gradual reutilisation of lactate as a substrate in aerobic metabolism by the cells of the ischaemic lesion is detected by a gradual decrease in the lactate signal.

Accordingly the observation of a decrease in lactate concentration in a region of the brain during oxygen challenge indicates the location of the ischaemic penumbra.

The change in lactate signal detected by MRI over time enables the result to be achieved. It may be possible, by titrating the oxygen delivery, to determine the oxygen concentration required to reduce the lactate signal gained from the target area. This should provide information on the presence of oxidative metabolism.

Various forms of susceptibility imaging are known. The methods of this invention may use any such susceptibility technique available in MRI and suitable to investigate the changes to signal consequential to the oxygen challenge step(s), e.g. a $T_2^*$ weighted magnetic resonance image scanning may be carried out.

The oxygen may be administered by inhalation or intravenously or in combination. Where the intravenous route is selected an oxygen carrier may be used. The oxygen carrier may be a perfluorocarbon or any other physiologically inert oxygen carrier.

Signal evaluation assumes that the baseline arises from the signal for the presence of lactate which is accumulated in cells of the brain undergoing anaerobic metabolism (anaerobic glycolysis).

So, when oxygen is present to initiate the Krebs cycle of aerobic metabolism and to convert the cellular metabolism from anaerobic to aerobic the said conversion manifests itself as a signal change in the sense that conversion to aerobic metabolism is recognisable as a decrease in signal.

In an embodiment of the present invention the method comprises the steps of: i) generating baseline imaging data of the target area of the organism; ii) administering oxygen to said organism; iii) generating imaging data in response to said administration of oxygen; iv) processing said imaging data to obtain data relating to the relative amounts of lactate present in said target area following administration of the oxygen, and correlating said data to the metabolic function of the target area.

Imaging data may be detected for lactate and/or lipid in the target area. Subtraction of the imaging data of the images obtained prior to oxygen administration from the image data obtained after oxygen administration results in an indication of a change in lactate or "lactate difference".

In another embodiment of the present invention, the method comprises the steps of: i) generating baseline imaging data of the target area of the organism; ii) administering oxygen to said organism; iii) generating imaging data following said administration of oxygen; wherein the imaging data so obtained relates to an indication of the relative amount of lipid and/or lactate present in the target area, and a change in image intensity following administration of oxygen indicates utilisation of lactate in the target area of the organism.

A novel MRI sequence may be utilised, specifically to image "changes in the lactate" signal. This sequence may be characterised by a combination of tailoring pulses to reduce water and fat saturation, optimising the frequency of pulses for the imaging of lactate and utilising a rapid acquisition relaxation enhanced (RARE) imaging method for measuring the magnetic resonance in the target area.

MRI techniques such as Rare $T_2$ imaging, diffusion weighted imaging (DWI), perfusion weighted imaging (PWI), 1H localised spectroscopy and lactate difference imaging (LDI) may be utilised with the methods of the present invention.

Data obtained may be processed to produce a metabolic map of the target area.

The administration of oxygen may be continued for a period sufficient to remove all lactate in the target area.

The signal representing lactate is identified from the obtained imaging data.

The observation of a reduction in the lactate signal after administration of free oxygen at low concentration doses indicates metabolic activity and therefore functional integrity in the target area.

A change in the lactate signal over time from positive to negative may be used to provide information on the rate of oxidative metabolism in a target area.

The target area may be selected from the group consisting of a region of tissue and an organ.

Oxygen may be administered once in a single dose.

Optionally, the oxygen may be administered by a slow drip injection of perfluorocarbons, or by way of an injected bolus.

The amount of perfluorocarbons administered by slow drip may range from about 300 ml to about 1000 ml ideally around 600 ml, and the amount of perfluorocarbons administered by bolus may range from about 50 ml to about 150 ml.

Alternatively, oxygen may be administered as a plurality of successive doses.

Oxygen may be administered in varying concentrations.

Optionally, the amount of oxygen administered may be linearly increased.

The amount of oxygen may be administered in increasing increments.

Optionally, a short period of time may be provided between each increment.

The administration of oxygen is in stages including a low level stage, and at least one stage at an elevated level in comparison with the "low level" stage.

The method may comprise a final low level stage or "rest phase".

The oxygen may be administered by a method selected from the group consisting of inhalation, intravenous delivery and combinations thereof.

Optionally, an oxygen carrier may be utilised in the intravenous delivery.

The oxygen carrier may be a physiologically inert oxygen carrier.

The oxygen carrier may be selected from the group consisting of perfluorocarbons.

The perfluorocarbon may be a stable emulsion of small particles having median diameter <0.2 µm.

The perfluorocarbon may be delivered as a bolus to facilitate determination of tissue perfusion information.

The imaging method may comprise $O_2T_2^*$ magnetic resonance image scanning.

Metabolic function may be determined in a patient affected by a condition selected form the group consisting of circulatory disorders including stroke, neural disorders including epilepsy (recurrent seizure), dementia and the like progressive brain dysfunctionality, autoimmune diseases including multiple sclerosis, neoplastic soft tissue dysfunctionality including cancers of the head and neck, lung cancers, gastrointestinal cancers, genitourinary cancers, lymphoma, and melanoma.

The metabolic function is determined and utilised as a means of differentiating tumour recurrence from tumour necrosis.

Another aspect of the present invention provides a diagnostic molecular magnetic resonance imaging method comprising the steps of a) administering oxygen to a patient whilst magnetic resonance imaging is carried out; b) generating images of the target area of interest of the patient's body before, during and after administration of oxygen; and c) processing said images to obtain data relating to the relative amounts of lactate and/or lipid in said target area following administration of oxygen, said data being indicative of the metabolic function of said target area and being useful in the diagnosis of disease.

Yet another aspect of the present invention provides a diagnostic molecular magnetic resonance imaging method comprising the steps of a) administering oxygen to a patient whilst magnetic resonance imaging is carried out; b) generating images of the target area of interest of the patient's body before, during and after administration of oxygen; and c) processing said images to obtain data relating to the relative amounts of lactate, water saturation and fat saturation in said target area over time following administration of oxygen, said data being indicative of the metabolic function of said target area and being useful in the diagnosis of disease.

The images obtained may be optimised so as to reduce the signal from water saturation and fat saturation in said target area.

Optionally, RARE imaging may be utilised.

The oxygen carrier may be a physiologically inert oxygen carrier.

The oxygen carrier may be selected from the group consisting of perfluorocarbons.

The target area may be selected from the group consisting of a region of tissue and an organ.

The target area may be the brain.

Another aspect of the present invention provides a method of determining effects of a therapeutic agent or prophylactic agent upon soft tissue or an organ in an organism using contrast magnetic resonance imaging (MRI), the method comprising the steps of: i) obtaining a first measurement of lactate in a target area of the organism; ii) administering oxygen to said organism; iii) obtaining a second measurement of lactate in a target area of the organism following said administration of oxygen; iv) processing said first and second measurements to obtain data relating to the relative amounts of lactate present in said target area following administration of the oxygen, and correlating said data to the metabolic function of the target area, v) repeating steps i) to iv) above in conjunction with simultaneous or sequential administration of the therapeutic agent, and evaluating the metabolic function to determine changes attributable to effects of the therapeutic agent.

Another aspect of the present invention provides an MRI Scanner configured to carry out any of the methods of the foregoing aspects.

Metabolic function in a target area of an organism may be determined using said MRI scanner which is configured to: i) generate baseline imaging data of the target area of an organism prior to an intervention; ii) obtain additional imaging data of the target area of an organism following said intervention; iii) process said imaging data to obtain data relating to the relative amounts of lactate present in said target area following said intervention, and correlate said data to the metabolic function of the target area.

The MRI scanner may be configured to detect lactate and/or lipid in the target area. Subtraction of the imaging data of the two images results in an indication of a change in lactate or "lactate difference".

The MRI scanner may be configured to execute a sequence for imaging "changes in the lactate" signal. This sequence may be characterised by a combination of tailoring pulses to reduce water and fat saturation, optimising the frequency of pulses for the imaging of lactate and utilising a rapid acquisition relaxation enhanced (RARE) imaging method for measuring the magnetic resonance in the target area.

The MRI scanner may also be configured to perform MRI techniques such as RARE $T_2$ imaging, diffusion weighted imaging (DWI), perfusion weighted imaging (PWI), 1H localised spectroscopy and lactate difference imaging (LDI).

The MRI scanner may process the data obtained to produce a metabolic map of the target area.

The intervention may be administration of oxygen.

The observation of a reduction in the lactate signal after administration of oxygen indicates metabolic activity and therefore functional integrity in the target area.

A reduction in the strength of the lactate signal over time may be used to provide information on the rate of oxidative metabolism in a target area.

The target area may be selected from the group consisting of a region of tissue and an organ.

Oxygen may be administered once in a single dose.

Alternatively, oxygen may be administered as a plurality of successive doses.

Oxygen may be administered in varying concentrations.

Optionally, the amount of oxygen administered may be linearly increased.

The amount of oxygen may be administered in increasing increments.

Optionally, a short period of time may be provided between each increment.

The administration of oxygen is in stages including a low level stage, and at least one stage at an elevated level in comparison with the "low level" stage.

The method may comprise a final low level stage or "rest phase".

The oxygen may be administered by a method selected from the group consisting of inhalation, intravenous delivery and combinations thereof.

Optionally, an oxygen carrier may be utilised in the intravenous delivery.

The oxygen carrier may be a physiologically inert oxygen carrier.

The oxygen carrier may be selected from the group consisting of perfluorocarbons.

The perfluorocarbon may be a stable emulsion of small particles having median diameter <0.2 µm.

The perfluorocarbon may be delivered as a bolus to facilitate determination of tissue perfusion information.

The imaging method may comprise $O_2T_2^*$ magnetic resonance image scanning.

BRIEF DESCRIPTION OF THE FIGURES

The present invention will now be described by way of example only and with reference to the accompanying figures in which:

FIG. 2 is a schematic diagram of a) the lactate difference MRI pulse sequence and how it works; and b) the method used to obtain lactate difference images;

FIG. 6 shows MRI images from an experiment using Lactate Difference Imaging in a rat following middle cerebral artery occlusion (MCAO). Panel (a) illustrates the region of severe ischaemic damage as identified by Diffusion Weighted Imaging (DWI) while panel (b) shows the area of hypoperfusion through the use of Perfusion Weighted Imaging (PWI). In order to detect changes in lactate following initiation of hyperoxia a baseline lactate image (c) was initially acquired following administration of 1.5 ml bespoke PFC. The animals' ventilation was changed to 100% oxygen (hyperoxia) during which a further lactate scan was acquired (d). Following this, ventilation was switched back to normoxic levels and a final lactate scan was acquired (e). By subtracting the image acquired during hyperoxia from the baseline image we generated a lactate change map (f) showing a decrease in the level of lactate (arrow) in an area approximating the DWI/PWI mismatch region (presumed penumbra). On removing the excess oxygen and returning to normoxic ventilation the lactate change map (g) (subtraction of e-d) showed a reverse of this decrease in lactate (arrow) in the corresponding region of the brain;

FIG. 9 shows the effect of administering bespoke PFC prior to hyperoxia following cerebral following middle cerebral artery occlusion (MCAO). FIG. 9a where the decrease in lactate peak in DWI/PWI mismatch region is evident when bespoke PFC (n=5) is administered prior to hyperoxia with this effect not seen in animals treated with saline (n=4) prior to hyperoxia. On returning the animal to normoxic ventilation (FIG. 9b) it was evident that the lactate peak increased to a greater level compared to pre hyperoxia levels in the saline treated animals while in PFC treated animals it only returned to its pre hyperoxia level;

FIG. 10 shows localised 1H spectra from (a) the ischaemic core region of the ipsilateral hemisphere and (b) the corresponding region of the contralateral hemisphere following MCAO in animals given 1.5 ml GOLD PFC prior to hyperoxia. It is evident that lactate remains unchanged in both regions during hyperoxia. This is likely to be due to tissue within the ischaemic core being unable to recover aerobic metabolism during hyperoxia; ie tissue no longer metabolically viable. The lack of effect in the contralateral hemisphere is likely to be a reflection of no increase in lactate level within this region of the brain acutely following stroke. Similar results were shown in animals treated with saline (data not shown).

DETAILED DESCRIPTION OF THE INVENTION

Figure 1:
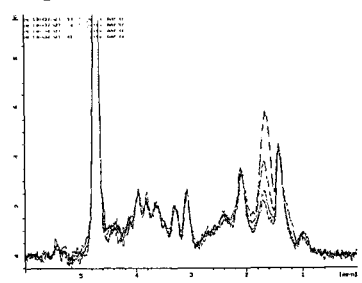
FIG. 1 shows localised 1H spectroscopy of rat after MCAO and effect of oxygen challenge. A) spectra from voxel placed with PWI/DWI mismatch region. B) Voxel placed in contralateral hemisphere.
Figure 1:
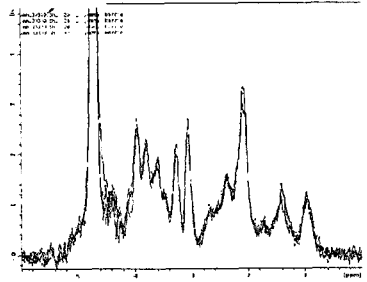
Figure 1:
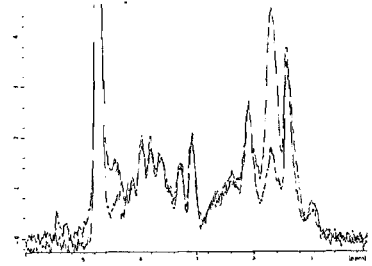
Figure 1:
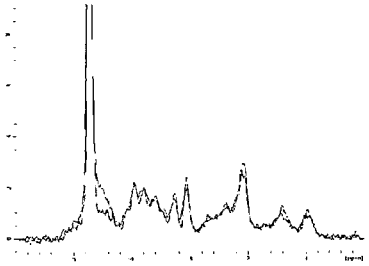

Data obtained since 1930 has suggested that lactate is the preferred substrate for aerobic oxidation for the purposes of bioenergetics by neurons. It is also well known that lactate increases within an ischaemic lesion and infarction. This occurs as a consequence of a shift to anaerobic metabolism due to the hypoxia/anoxia.

Anaerobic metabolism (glycolysis) is very inefficient and can only provide approximately 6% of the potential energy from glucose. By contrast, the Krebs cycle provides 94% of the available energy from glucose. Therefore, the integrity of the Krebs cycle is essential for cell survival.

Thus, following an occlusive insult of an organ in the human body such as an ischaemic stroke in the brain, any technique able to demonstrate a functioning Krebs cycle within the ischaemic lesion would also thereby identify tissue that is surviving or has the potential to survive.

An increase in lactate within ischaemic/infracted brain has been shown by magnetic resonance spectroscopy following cerebral infarction due to failure of aerobic metabolism (Berkelback van der Sprenkel J W et al 1988, Fenstermacher M J and Naryana P A 1990 and Houkin K 1990).

Additionally, the preferred substrate for neuronal metabolism is lactate, which in the brain is produced primarily by the astrocytes. Therefore, demonstrating the production of lactate and its utilisation would indicate metabolic integrity of the neurons and astrocytes and therefore their potential to survive the insult following cerebral infarction.

To date, MRS techniques have only been able to show the presence of lactate in a tissue and an increase in such lactate over time following cerebral infarction. There are currently no techniques known in the art able to demonstrate the temporal utilisation of lactate with oxygen and thus demonstrate the penumbra after cerebral infarction.

The present invention provides a novel imaging technique that has demonstrated lactate metabolism within brain tissues identified as potential penumbra in a rat stroke model.

Brain tissues accumulate lactate within ischaemic/infracted brain tissues. This occurs due to the lack of oxygen, as oxygen is essential for aerobic metabolism. This accumulation of lactate within an infarct was initially demonstrated in a case report (Berkelback van der Sprenkel J W et al 1988).

Subsequent animal and human studies have shown an acute increase in rise in lactate, which persists for a few days after cerebral infarction (Fenstermacher M J and Naryana P A 1990 and Hokkaido Igaku Zasshi 1990).

It has now been found that identification of metabolically functioning neurons and thus the penumbra is possible in real time utilising a technique developed to increase the amount of oxygen delivered to the ischaemic tissues and to monitor a temporal change in lactate concentrations.

Increasing the amount of oxygen can be achieved by increasing the percentage of inhaled oxygen. Normally the percentage of oxygen in air is 21% and at sea level the partial pressure ($pO_2$) is about 160 mm of Hg. Therefore, increasing the percentage of oxygen and the $pO_2$ would increase the amount of oxygen carried by blood. However, haemoglobin is fully saturated while breathing air and so the increased oxygen during hyperoxia, is carried by the plasma. However, this is a very inefficient as the amount of oxygen carried by every mm Hg increase is only 0.003 ml (Law and Bukwirwa, 1999).

Therefore, only small amounts of oxygen would be delivered to ischaemic tissues hyperoxia and so will take a long time to detect any change in lactate to identify the penumbra. Time is of the essence following a cerebral infarction, and therefore reducing detection time is paramount.

To achieve this PFC has been utilised in the methods of the present invention to carry increased oxygen. 100 ml Perflorodecalin can carry 49 ml of oxygen at standard temperature and pressure. This is many fold higher than that possible with plasma.

The methods of the present invention also consist of a novel MRI sequence to image lactate.

In a general embodiment of the method varying amounts of oxygen are administered to an organism whilst monitoring magnetic susceptibility, e.g. $T_2^*$ weighted magnetic resonance image ($O_2T_2^*$) scanning is carried out. The oxygen may be administered via inhalation using a face mask, or intravenously using an oxygen carrier, or in combination. Tissues which are metabolically active utilise oxygen, resulting in a gradual decrease in the presence of lactate.

In the method of the present invention, MRI scanning of the brain will reveal an accumulation of lactate in ischaemic brain cells as a result of glycogenolysis and/or anaerobic glycolysis metabolism. Lactate is gradually utilised as a substrate for aerobic glycolysis upon the availability of oxygen, thus reducing the MRI signal gained from lactate. In non ischaemic tissue with functional aerobic metabolism, little lactate will be observed at baseline and little change will be observed upon oxygen challenge. In ischaemic tissue, a large build-up of lactate will be observed at baseline. Upon oxygen challenge, areas of tissue showing a sharp decrease in lactate signal would indicate metabolic integrity of the neurons and astrocytes and therefore their potential to survive the insult following cerebral infarction. This lactate reduction reduces the strength of the signal. Depending on the metabolic activity of the tissue being examined a pronounced change in the signal, specifically a reduction in the strength of the signal, will be observed with increased oxygen delivery (titration) and is used to produce a semi-quantitative metabolic map of the tissue or organ.

In tissues with no metabolism (i.e. dead tissue) there will be no facility to convert lactate to pyruvate and thus to enter the Krebs cycle. Thus there will be no decrease detected in the lactate signal from such tissues due to functional impairment.

In-Vivo MRI and MRS Experiments and a Novel Lactate Difference Imaging Method

In-vivo MRI experiments were performed on anaesthetised rats following a middle cerebral artery occlusion (MCAO). The measurements included RARE $T_2$ imaging, diffusion weighted imaging (DWI), perfusion weighted imaging (PWI), 1H localised spectroscopy and lactate difference imaging (LDI).

Localised 1H spectroscopy and the effect of oxygen challenge.

The first experiment used a standard localised spectroscopy sequence (PRESS) to acquire 1H spectra. One voxel was placed in the presumed penumbral region (as indicated by DWI/PWI mismatch), a second voxel was placed in the normal contralateral hemisphere (see FIG. 1)

On giving a challenge of 100% inhaled oxygen the lactate peak in the penumbral region showed a significant decrease (FIG. 1a). Importantly, no other metabolites in the spectra showed any change with oxygen. In the contralateral region, the lactate peak remained unchanged (FIG. 1b). On returning to 100% inhaled air, the reduced lactate peak in the penumbra, increased back to previous level (FIG. 1c).

Lactate Difference Imaging

It was desirable to image the region where the changes in lactate occurred during an oxygen challenge, as these regions could define the ischaemic penumbra.

Previous attempts at imaging lactate have used standard Chemical Shift Imaging (CSI), where a full 1H NMR spectra is acquired for an array of voxels. This technique suffers from very low spatial resolution and long acquisition times.

Also, spectral editing techniques eg via J coupling or multiple quantum coherence effects (Reese 1995, Pickup 2008) have been used. Again, these techniques suffer from significant lose of signal, limiting the spatial and temporal resolution of acquired images.

Hence, a novel sequence has been utilised, specifically to image "changes in the lactate" signal. This sequence may be described by the block diagram shown in FIG. 2a, comprising a combination of tailoring pulses to reduce water and fat saturation, optimising the frequency of pulses for the imaging of lactate and utilising a rapid acquisition relaxation enhanced (RARE) imaging method for measuring the magnetic resonance in the target area.

Figure 3:
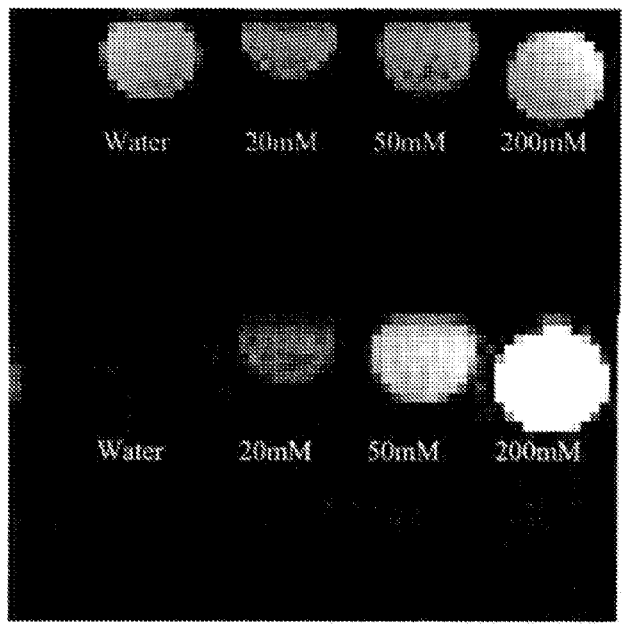
FIG. 3 contains imaging using the lactate MRI sequence. Top shows images of phantoms using 1H water signal. Bottom shows images using lactate $CH_3$ resonance signal.

The sequence was tested on phantoms made with a range of concentrations of lactate, from which it can be seen that the sequence is able to successfully image a low concentration of lactate, without contamination from the much larger water signal (i.e. no image can be seen in the phantom comprising water only). See FIG. 3.

In-vivo, the sequence will may be utilised to image both lactate and lipid signal, as their resonance frequencies overlap.

The sequence may be used to specifically image "changes in lactate" caused by an oxygen challenge. The oxygen challenge has no effect on the lipid concentration but reduces the lactate concentration. Thus, subtraction of the two images results in the "change in lactate" or "lactate difference" images (see FIG. 4b).

The present technique is more efficient than either CSI or lactate editing methods, as no MRI signal is wasted in editing out the lipid signal, and thus, allowing high spatial resolution to be imaged, even at the low lactate concentrations.

The method herein described provides a scanning paradigm which will allow semi-quantitative measures of brain metabolism. This paradigm may involve variation of the inspired oxygen during the scanning procedure. This may take the form of the administration of multiple stable levels of oxygen concentration, typically on an incremental basis, or constantly varying oxygen concentration levels (e.g. linearly increasing or decreasing the concentration level). By analysing the variation of the lactate signal with changing levels of administered oxygen it is possible to produce semiquantitative metabolic maps.

Figure 4:
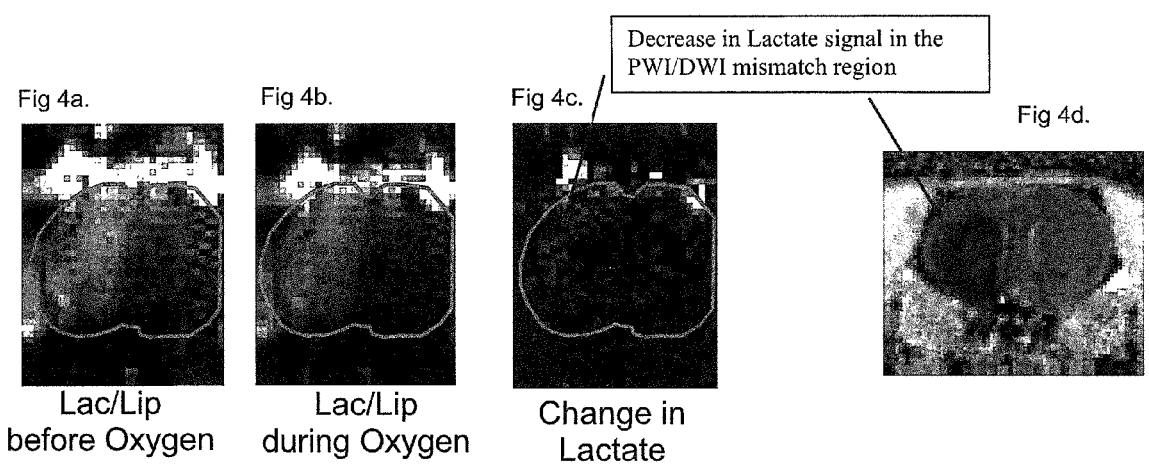
FIG. 4 contains in-vivo MRI images of rat following MCAO. A) lactate-lipid image before $O_2$; B) lactate-lipid image during Oxygen challenge; C) lactate difference images (ie B-A); and D) mismatch region from DWI/PWI.
Figure 5:
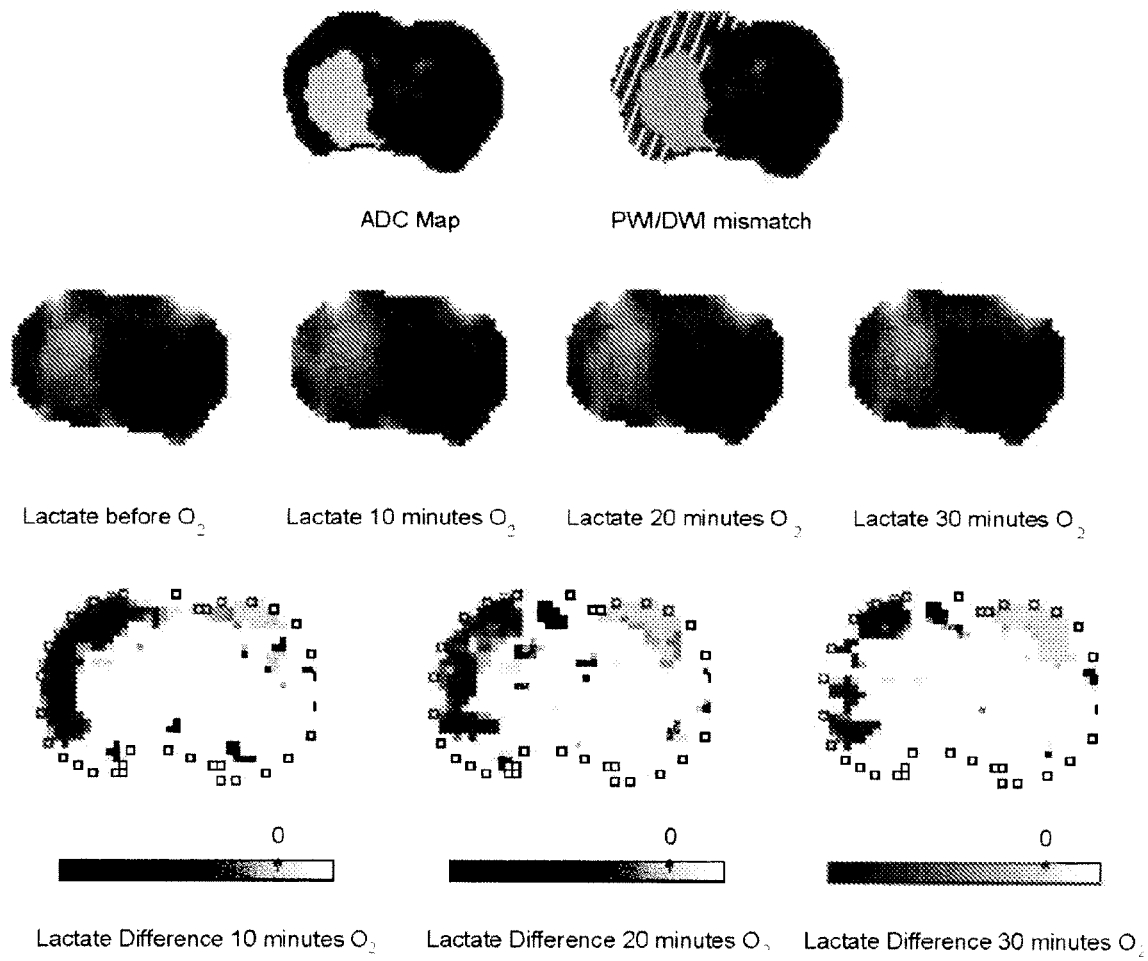
FIG. 5 shows in-vivo MRI images of rat following MCAO. 100% Oxygen used as the challenge.
Figure 7:
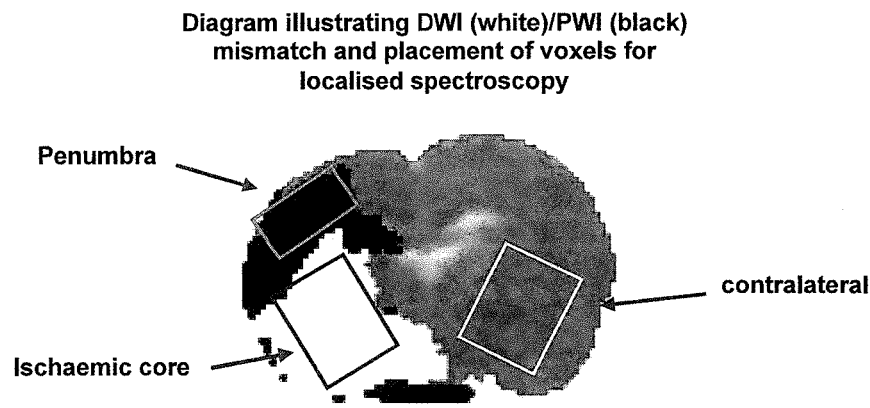
FIG. 7 illustrates the placement of the voxels. One voxel was placed in the region of the presumed penumbra (DWI/PWI mismatch) with other voxels placed in the ischaemic core region (dead tissue) and the normal contralateral hemisphere.
Figure 8:
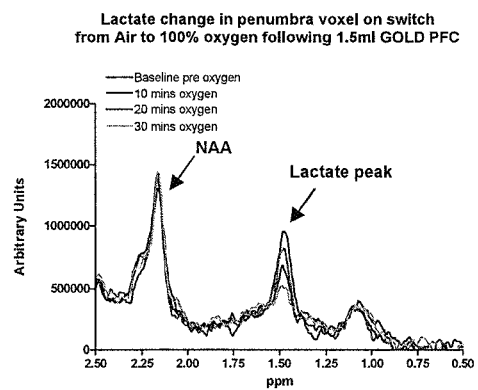
FIG. 8 shows localised 1H spectra taken from the DWI/PWI mismatch region following MCAO with N-Acetyl Aspartate (NAA) and lactate peaks labelled. It is evident that the lactate peak is decreased in the animal given 1.5 ml bespoke PFC (a) during hyperoxia with no such decrease in the animal receiving saline (b)
Figure 8:
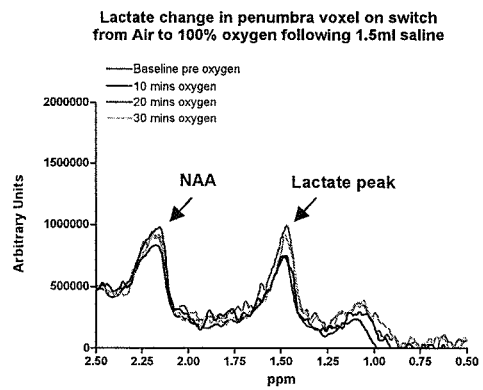

The oxygen may be administered via a face mask. This technique is easy and generally acceptable to patients. However a technical problem with this route of administering oxygen is that it can result in large susceptibility artifacts in the inferior frontal and inferior temporal lobes, due to replacement of air within the paranasal sinuses with paramagnetic oxygen (FIG. 4). Therefore the inferior frontal and temporal lobes may not always be assessed by delivering oxygen though the oro-nasal route. In addition it is difficult to fine tune the amount of oxygen administered by a mask. Even if the patient is administered 100% oxygen via the inhalation route the plasma blood levels are only increased by some 5-6%. Consequently the signal change observed in response is also relatively small.

Therefore, another route of administering oxygen to obviate this problem would be advantageous. Using the intravenous route for the administering of drugs is routine in clinical practice and ideal for this requirement. There are known blood replacement products or blood expanders which include oxygen carriers offering the capability of delivering oxygen for release to tissues. It is envisaged that any such suitable oxygen carrier agent, which may be administered intravenously could be considered for the purpose of providing an alternative to the oro-nasal route. One particular type of oxygen carrier considered to be suitable for this purpose would be perfluorochemicals.

Perfluorochemicals are chemically inert synthetic molecules that consist primarily of carbon and fluorine atoms, and are clear, colourless liquids. They have the ability to physically dissolve significant quantities of many gases including oxygen and carbon dioxide. At present they are commonly used as "blood substitutes" during surgery. Perfluorochemicals are hydrophobic, and are therefore not miscible with water.

Perfluorochemicals thus have to be emulsified for intravenous use. With sophisticated technology, it is possible to generate a stable perfluorocarbon emulsion with exceptionally small particles (median diameter <0.2 μm) (Keipert PE 10). Oxygen transport characteristics of perfluorocarbon emulsions are fundamentally different from those of blood. Perfluorocarbon emulsions are characterized by a linear relationship between oxygen partial pressure and oxygen content, in contrast to blood which exhibits a sigmoid oxygen dissociation curve (Keipert PE 10). Therefore the oxygen carrying capacity is directly proportional to $PO_2$ and this means that the amount of oxygen carried by perfluorocarbons can be varied by varying the $PO_2$. The oxygen transport characteristics and ability to vary the oxygen carrying capacity, makes perfluorocarbons ideal to use as an agent to carry oxygen in the present method. As the oxygen carrying capacity can be varied stratification of the tissues based on their metabolic rates can be obtained. The intravenous route is routinely used in clinical practice and will not cause the artifacts seen when oxygen is administered using a face mask. The first perfluorocarbon used as a compound to carry and deliver oxygen was Fluosol™, approved in 1989 by FDA. However this product manufactured by Green Cross needed to be frozen for storage and thawed before use. An alternative product Oxygent™ is not frozen but is in a ready to use form.

It is expected that any suitable perfluorocarbon or physiologically inert oxygen carrier commercially available, and any of those, or others that may yet be made available could be used for the purpose of oxygen delivery in the present method.

The $PO_2$ of air at normal atmospheric pressure is 160 mm of Hg and the percentage of oxygen is 21%. This means that as the perfluorocarbon passes through the lungs, the oxygen would bind to it and the amount of oxygen within the bolus of perfluorocarbon could be up to 21% (depending on the degree of mixing of blood and agent which takes place). Since the binding of oxygen to perfluorocarbons is 1:1, if the inhaled oxygen is increased to 30% the oxygen carrying of the perfluorocarbon could be up to 30% and further increases would result in a corresponding increase.

The intravenous route with i.v. perfluorocarbon results in an $O_2$ concentration of up to 21% compared to the inhalational route alone which achieve about 3-4%.

However the concentrations of oxygen can be even further increased by the inhalation of higher concentrations of $O_2$ during the intravenous injection of the perfluorocarbons. At concentrations of up 60% oxygen, artefacts are not present due to the paramagnetic effect of free oxygen within the nasal cavities and/or the air sinuses. Thus, in one embodiment the method is carried out via intravenous injection of an oxygen carrying compound whilst the patient breathes air. However, if required, the concentration of air can be increased to make the test more sensitive, by the supplementation of higher concentrations of oxygen through inhalation.

A suitable method for performing magnetic resonance imaging scan illustrative of the invention comprises:

1) Patient is positioned in an MRI scanner

2) Scanning starts. This sequence collects whole brain scans (or any other part of the body under investigation), repeatedly over the course of the study resulting in a number of volumes providing temporal information. This scan runs continuously until step 8 is completed.

3) The scan proceeds for a specified time without any medium injection or oxygen inhalation. This provides baseline data for future image analysis.

4) A specified amount of metabolic bio-tracer is injected at a specified rate.

5) Depending on the particular protocol the patient may or may not inhale oxygen at an increased partial pressure for the duration of the injection and for a short period following the injection.

6) After the injection (and inhalation if required) a period of no injection or oxygen inhalation is undertaken, providing further baseline data and allowing the metabolic bio-tracer dilute within the cardiovascular system.

7) Depending on the protocol steps 4 and 5 are repeated either with a different amount of bio-tracer, a different injection time or a different partial pressure of inhaled oxygen. It is possible that more than one of these parameters may be varied at any one time.

8) Depending on the protocol, steps 4-7 are repeated a specified number of times, each time with specified variations in the parameters described in step 7.

9) The data from this scan is analysed using image analysis software to provide quantitative or qualitative measures of the oxidative metabolic activity within the tissues being scanned.

10) Optionally it may also be possible to track the passage of the oxygenated perfluorochemicals to provide tissue perfusion information. This would require the perfluorochemicals to be injected by a bolus method.

The amounts of medium injection and/or oxygen inhalation may be any of the following illustrative protocols, each of which could take up to a minute, and may be optionally repeated or used in sequence. If repetitions are required these may be optionally spaced apart by from one to several minutes preferably 1-2 minutes apart.

Administration of Oxygen:

Optionally, the oxygen may be administered by a slow drip injection of perfluorocarbons, or by way of an injected bolus. The amount of perfluorocarbons administered by slow drip may range from about 300 ml to about 1000 ml ideally around 600 ml, and the amount of perfluorocarbons administered by bolus may range from about 50 ml to about 150 ml.

A. The amount of perfluorocarbon injection may be from 10 ml to 150 ml, breathing air. The oxygen carried by perfluorocarbon would be up to 21% and the amount of free oxygen in the blood is almost 0 and so the difference would be up to 21%.

B. The amount of perfluorocarbon injection may be from 10 ml to 150 ml, breathing 30% oxygen. The oxygen carried by perfluorocarbon would be up to 30% and the amount of free oxygen in the blood would be about 1.3%. The difference between these two would be approximately 30%−1.3%=28.7%. C. The amount of perfluorocarbon injection may be from 10 ml to 150 ml and breathing 40% oxygen. The oxygen carried by perfluorocarbon would be up to 40% and the amount of free oxygen in the blood would be about 2.6%. The difference between these two would be approximately 40%−2.6%=37.4%.

D. The amount of perfluorocarbon injection may be from 10 ml to 150 ml and breathing 50% oxygen. The oxygen carried by perfluorocarbon would be up to 50% and the amount of free oxygen in the blood would be about 3.9%. The difference between these two would be approximately 50%−3.9%=46.1%.

E. The amount of perfluorocarbon injection may be from 10 ml to 150 ml and breathing 60% oxygen. The oxygen carried by perfluorocarbon would be up to 40% and the amount of free oxygen in the blood would be about 5.2%. The difference between these two would be approximately 60%−5.2%=54.8.4%.

Any one of the above steps (A-E) could take up to one minute. However for most examinations, only one of such oxygen administration steps would be required so the complete data gathering or diagnostic examination could be completed in one minute. In some clinical situations, more than one repetition might be needed, but it is unlikely that much benefit could be obtained by exceeding 10 repetitions. There is no theoretical time period to wait between repetitions, if this is considered desirable, a short delay would not interfere with the procedure, and in practice it may be of the order of 1-2 minutes.

In addition to being useful for modelling the metabolic function of tissues, the described method can be used to assess the metabolic function of normal and diseased tissues and organs. These can be compared to assist in the diagnosis of disease states and analysis of tissue and organ states. Due to the general applicability of the method the types of disease which can be investigated and diagnosed are not limited, but for illustrative purposes may include ischaemic incidents such as stroke; epilepsy; dementia, including Alzheimer's disease; Multiple Sclerosis; cancer and cardiac disease.

Stroke is the third most common cause of death and the largest single cause of severe disability. The cost for society is also very high and the average cost per patient across Europe is about 15,000 Euro per patient during the first year. The therapeutic strategies to treat stroke aim to limit cerebral ischaemia by early reperfusion and interference with the patho-biochemical cascade leading to ischaemic cell death (Heiss et al). Therapy can only be effective if there is viable and potentially salvageable brain tissue. The term "ischaemic penumbra" is used to define this viable brain tissue (Baron, Benard Schaller). Ideally one would want to stratify the injured tissue along haemodynamic, functional and metabolic dimensions (Hakim A M). The potential time window for the various treatment options is variable, since the penumbra may last up to 48 hours in some patients (Heiss W D and Marchal M E). The time window for, starting reperfusion-based treatments is very short (thrombolytic measures), longer for neuroprotection and longer still for antioxidant and anti-apoptotic measures. For all these treatment options it is first necessary to establish the presence and extent of the penumbra. Imaging is the only direct way of assessing the penumbra. Positron Emission Tomography (PET) imaging is considered the reference standard for the evaluation of the pathophysiological changes in early stroke (Baron JC 4). However, its use in clinical practice is not practical, as it is complex, costly and not readily available.

A pilot study using a rat model has shown tissues responding to the oxygen challenge within the DW abnormality at two hours and three hours after occlusion. DW abnormality seen after vascular occlusion also contains the Penumbra. Therefore the tissues within the ADC boundaries, which responded in a similar time course as normal tissues to the oxygen challenge, are metabolically active and so could be the ischaemic penumbra. See FIGS. 5 to 10.

A pilot study in stroke patients has also been conducted and suggests the technique is easy to translate in this clinical situation.

Epilepsy

Epilepsy or recurrent seizure is a common disorder with a prevalence of approximately 1:130 in the UK. Most adult epilepsies are focal. About 30% are not brought under satisfactory control using drug treatment and increasingly surgical treatment is being considered. In these cases it is very important to identify the seizure focus for surgery. Patients are investigated prior to surgery with EEG, structural MRI, SPECT and PET. EEG is used to pick up the abnormal electrical activity generated by the seizure focus. However surface EEG studies cannot accurately localise the abnormality within the brain. Nevertheless this can be done by placing electrodes into the brain, although this carries risks due to the invasive nature of the technique. Studies have shown altered metabolism within the seizure focus. During the ictus there is increased metabolism and blood flow and this reduces post-ictally. Therefore, techniques with the ability to anatomically demonstrate altered blood flow such as SPECT and altered metabolism such as PET 18FDG are also used to demonstrate the seizure focus. However the main drawbacks, common to both these techniques are the use of radio-isotopes and relatively limited spatial resolution. In addition the cost of PET scans is very high.

Using the above described method the inventors believe it would be able to non-invasively demonstrate the seizure focus. The advantages of MRI are that it does not use ionising radiation, has higher spatial resolution, it is ubiquitous and has a lower cost than PET. A further pilot study is being conducted using this technique on selected epilepsy patients.

Dementia

Dementia, a progressive brain dysfunction, leads to a gradually increasing restriction of daily activities. Dementia not only affects patients, but also those surrounding them, as most patients require care in the long-term. The most well known type of dementia is Alzheimer's disease. The Alzheimer's Society estimates that there are currently over 750,000 people in the UK with dementia. Current theories on the pathogenesis of the cognitive signs and symptoms of Alzheimer's disease attribute some of them to a deficiency of cholinergic neurotransmission. Donepezil hydrochloride a drug used in Alzheimer's disease is postulated to exert its therapeutic effect by enhancing cholinergic function and improve cognitive performance in patients for unto a year. This drug treatment is expensive and there are many other causes of dementia, for which this treatment is not effective. Therefore, diagnosis of this condition is important and this is currently achieved using SPECT or PET scans, which show reduced blood flow and metabolism in the temporal and parietal lobes of the brain. It is postulated that this specific pattern could also be detected by the methods of the present invention.

Multiple Sclerosis

MS is thought to be an autoimmune disease that affects the central nervous system (CNS). The CNS consists of the brain, spinal cord, and the optic nerves. Surrounding and protecting the nerve fibers of the CNS is a fatty tissue called myelin, which helps nerve fibers conduct electrical impulses. Myelin not only protects nerve fibers, but makes conduction possible. When myelin or the nerve fibre is destroyed or damaged, the ability of the nerves to conduct electrical impulses to and from the brain is disrupted, and this produces the various symptoms of MS. MRI scans are the most sensitive way of detecting the lesions in MS. However plain MRI scans cannot differentiate actively inflamed lesions from older healed lesions. Gadolinium enhanced scans can demonstrate actively inflamed lesions as the blood brain barrier is disrupted. Since the metabolism of an active lesion would be different from the older healed lesions, it is postulated that methods of the present invention could demonstrate the actively inflamed lesions on this basis.

Cancer

Over 270,000 new patients are diagnosed with cancer annually in the UK. Cross-sectional imaging using MRI and CT, currently have a central role for the management of patients with malignant disease. This role includes initial diagnosis and staging, monitoring response to treatment and recognition of complications. The use of size as a criteria of lymph nodal involvement has its limitations. Tumour tissues have a higher level of metabolism and this has been used to detect cancer dissemination within lymph nodes, by combing structural CT scans with—PET 18FDG. It is believed that the above described technique will demonstrate tissues that are metabolically different, and with high resolution structural MRI scans, can replace PET-CT staging cancer. This will have an impact not only on costs but also the ability to deliver results quickly, as MRI scanners are ubiquitous and the technique will be easy to translate clinically. As MRI imaging does not use ionising radiation, the response of treatment can be more closely monitored, since there no limitations on the number of times the patient or the time intervals before imaging can be repeated. Therefore the present method could be used in staging head and neck cancers, lung cancers, gastrointestinal cancers, genitourinary cancers, lymphoma and melanoma. This ability to monitor development or progression of cancer from a primary tumour to metastases by targeting particular tissue (e.g. lymph nodes) or organs (e.g. liver) is a significant development in the care of cancer sufferers. The method can also be used in differentiating tumour recurrence from tumour necrosis in brain gliomas.

Cardiac Imaging

In the U.K. 140,000 people die every year from heart disease. Narrowing of the coronary arteries can result in insufficient blood supply to the heart, especially at times of physical or emotional stress. The narrowing of the arteries is due to deposition of cholesterol plaques on the inner wall of the artery. The lack of oxygenated blood due to coronary artery disease causes the heart muscle to go into anaerobic metabolism, producing a cramp-like pain known as angina. The lack of oxygen for more than a short period causes ischaemia and/or muscle cell death. Computed tomography coronary angiography (CTCA) is a technique for non-invasive detection of the narrowing of a blood vessel (coronary stenosis). CTCA is an excellent tool to rule out relevant coronary artery disease, but not every plaque or lesion of the coronary arteries causes significant reduction of blood flow to the heart. Myocardial perfusion (blood flow) imaging using single photon emission computed tomography (SPECT) is an established method for assessing the physiologic significance of coronary lesions in patients with chest pain. Combining theses two imaging modalities of the heart has provided both anatomical and physiological information for better management of cardiac ischaemia. Now cardiac MRI can also provide an accurate picture of the heart. It can capture the heart beating in real time by imaging up to 50 frames per second in a sequence triggered by an electrocardiogram (EKG) machine. These capabilities allow us to see the coronary arteries in enough detail to determine whether plaque accumulation or blockages have occurred. Cardiac MRI can also determine the extent of muscle damage following a heart attack, because MRI has good soft tissue contrast and so can identify the subtle differences between normal and abnormal heart muscles. However this is still information is still only structural. Ideally one would require information that would be, able to stratify affected tissues on the basis of function. Cardiac tissues that are functionally active will have higher metabolism and therefore imaging of the heart using the current method can stratify tissues that are normal, ischaemic and infracted.

Advantageously the method of the present invention is envisaged to have application in the management of many common diseases. A benefit of the procedures described herein lies in the fact that the data relating to metabolic function (or dysfunction) of tissue is available in real time, yielding valuable information about viable tissue, and enabling a quick decision to be taken if an intervention or procedure has to be considered as a consequence of a diagnosis made on the base of the data gathered.

The invention finds utility in supporting research into disease and degenerative disorders and in supporting diagnosis and treatment of conditions which may be life threatening or otherwise reduce the quality of life of an individual. Thus the invention is applicable in monitoring stages of cancer, e.g. for assessing metastases, typically spread of cancer from a primary tumour to lymph nodes or migration through another circulatory system or into an organ such as the liver.

The invention also finds utility in screening of drugs, and assessment of effects of administration of a therapeutic or prophylactic agent upon soft tissue or an organ by carrying out the method of the first or second aspects described hereinbefore in conjunction with simultaneous or sequential administration of said agent, and evaluating the metabolic function to determine changes attributable to effects of said agent.

Further modifications and improvements may be added without departing from the scope of the invention herein described.

The invention claimed is:
1. A method of imaging the ability for aerobic metabolism in a target area of an organism using magnetic resonance spectroscopic imaging (MRSI), the method comprising the steps of:
  i) intravenously administering an oxygen carrier to said organism;
  ii) baseline imaging the target area of the organism using MRSI;
  iii) calculating a first baseline lactate imaging signal from said baseline imaging across the target area of the organism;
  iv) after said baseline imaging, administering supplemental oxygen to said organism by inhalation;
  v) second imaging the target area of the organism using MRSI following administration of said supplemental oxygen by inhalation;
  vi) calculating a second lactate imaging signal from said second imaging across the target area of the organism;
  vii) comparing said first baseline lactate imaging signal and said second lactate imaging signal wherein a significant difference between the first baseline lactate imaging signal and the second lactate imaging signal relates to a relative change in lactate concentration across said target area following administration of said supplemental oxygen by inhalation,
  wherein the MRSI used comprises a sequence of pulses which suppress the water and fat signal and optimise the lactate signal, and
  viii) identifying tissue with no significant difference between the first baseline lactate imaging signal and the second lactate imaging signal as tissue with normal aerobic metabolism;
  ix) identifying tissue with: (i) a higher relative first baseline lactate imaging signal than tissue with normal aerobic metabolism, and (ii) with either: no significant difference between the first baseline lactate imaging signal and the second lactate imaging signal; or an increase in the lactate signal from the first baseline lactate imaging signal to the second lactate imaging signal as non-viable ischemic or infarcted tissue with no ability for aerobic metabolism; and
  x) identifying tissue having a decrease in lactate signal from the first baseline lactate imaging signal to the second lactate imaging signal as metabolically viable ischemic tissue with an ability for aerobic metabolism.

2. The method of claim 1, wherein the MRSI sequence is characterised by a combination of tailoring pulses to reduce water and fat saturation, optimising the frequency of pulses for the imaging of lactate and utilising a rapid acquisition relaxation enhanced (RARE) imaging method for measuring the magnetic resonance in the target area.

3. The method of claim 1, wherein the MRSI further comprises one or more techniques selected from RARE $T_2$ imaging, diffusion weighted imaging (DWI), perfusion weighted imaging (PWI), 1H localised spectroscopy and lactate difference imaging (LDI).

4. The method of claim 1, wherein data obtained is processed to produce a metabolic map of the target area.

5. The method of claim 1, wherein the administration of oxygen is continued for a period sufficient to remove all lactate in the target area.

6. The method of claim 1, wherein the target area is selected from the group consisting of a region of tissue and an organ.

7. The method of claim 1, wherein in step iv) oxygen is further administered by intravenous delivery.

8. The method of claim 1, wherein the MRSI comprises $O_2T_2^*$ magnetic resonance image scanning.

9. The method of claim 1, wherein the metabolic function is determined in a patient affected by a condition selected form the group consisting of circulatory disorders including stroke, neural disorders, progressive brain dysfunctionality, autoimmune diseases, neoplastic soft tissue dysfunctionality, lung cancers, gastrointestinal cancers, genitourinary cancers, lymphoma, and melanoma.

10. The method of claim 1, wherein the metabolic function is determined and utilised as a means of differentiating tumour recurrence from tumour necrosis.

11. The method of claim 1 further comprising the steps of:
  repeating steps i) to vii) in conjunction with simultaneous or sequential administration of a therapeutic or prophylactic agent, and evaluating the metabolic function to determine changes attributable to effects of the therapeutic or prophylactic agent;

to determine effects of the therapeutic agent or prophylactic agent upon soft tissue or an organ in an organism.

12. The method of claim 1, wherein the intravenous administration of the oxygen carrier to the organism (step (i)) occurs after calculating the baseline lactate imaging signal across the target area of the organism (step (iii)).

13. A method of imaging the ability for aerobic metabolism in the brain following neurological trauma of an organism using magnetic resonance spectroscopic imaging (MRSI), the method comprising the steps of:
   i) intravenously administering an oxygen carrier to said organism;
   ii) baseline imaging the target area of the organism using MRSI;
   iii) calculating a first baseline lactate imaging signal from said baseline imaging across the brain of the organism;
   iv) after said baseline imaging, administering supplemental oxygen to said organism by oxygen inhalation;
   v) second imaging the target area of the organism using MRSI following administration of said supplemental oxygen by inhalation;
   vi) calculating a second lactate imaging signal from said second imaging across the brain of the organism;
   vii) comparing said first baseline lactate imaging signal and said second lactate imaging signal wherein a significant difference between the first baseline lactate imaging signal and the second lactate imaging signal relates to the relative change in lactate concentration across the brain following administration of said supplemental oxygen by inhalation,
   wherein the MRSI used comprises a sequence of pulses which suppress the water and fat signal and optimise the lactate signal, and
   viii) identifying tissue of the brain with no significant difference between the first baseline lactate imaging signal and the second lactate imaging signal as tissue of the brain with normal aerobic metabolism;
   ix) identifying brain tissue with: (i) a higher relative first baseline lactate imaging signal than tissue with normal aerobic metabolism; and (ii) with either: no significant different between the first baseline lactate imaging signal and second lactate imaging signal; or an increase in the lactate signal from the first baseline lactate imaging signal to the second lactate imaging signal as non-viable ischemic or infarcted brain tissue with no ability for aerobic metabolism; and
   x) identifying having a decrease in lactate signal from the first baseline lactate imaging signal to the second lactate imaging signal as viable ischemic brain tissue with an ability for aerobic metabolism.

14. The method of claim 13, wherein the intravenous administration of the oxygen carrier to the organism (step (i)) occurs after calculating the baseline lactate imaging signal across the brain of the organism (step (iii)).

15. The method of claim 13 wherein the neurological trauma is stroke.

* * * * *